United States Patent
Rohdewald et al.

(12)

(10) Patent No.: US 6,565,851 B2
(45) Date of Patent: May 20, 2003

(54) RELIEVING SYMPTOMS OF ERECTILE DYSFUNCTION WITH PROANTHOCYANIDINS

(75) Inventors: Peter Rohdewald, Münster (DE); Victor Ferrari, Feutersoey (CH)

(73) Assignee: Horphag Research Limited, Geneva (CH)

( * ) Notice: Subject to any disclaimer, the term of this patent is extended or adjusted under 35 U.S.C. 154(b) by 63 days.

(21) Appl. No.: 09/865,189

(22) Filed: May 24, 2001

(65) Prior Publication Data

US 2002/0037862 A1 Mar. 28, 2002

Related U.S. Application Data

(60) Provisional application No. 60/207,520, filed on May 26, 2000.

(51) Int. Cl.$^7$ .............................................. A61K 39/385
(52) U.S. Cl. ..................... 424/195.1; 424/776; 514/456
(58) Field of Search .............................. 424/195.1, 769, 424/770, 775, 776; 435/191; 514/456

(56) References Cited

U.S. PATENT DOCUMENTS

| | | | | |
|---|---|---|---|---|
| 4,698,360 A | * | 10/1987 | Masquelier | ................ 514/456 |
| 5,695,761 A | * | 12/1997 | Denhardt et al. | ........ 424/184.1 |
| 5,720,956 A | | 2/1998 | Rohdewald | .............. 424/195.1 |
| 6,007,824 A | * | 12/1999 | Duckett et al. | .......... 424/195.1 |
| 6,297,273 B1 | * | 10/2001 | Romanczyk, Jr. | ........... 514/456 |
| 6,423,743 B1 | * | 7/2002 | Romanczyk, Jr. | ........... 514/456 |
| 6,469,053 B1 | * | 10/2002 | Romanczyk, Jr. et al. | .. 514/456 |

FOREIGN PATENT DOCUMENTS

| | | | |
|---|---|---|---|
| DE | 19845314 | * | 4/2000 |
| DE | 19845314 A1 | | 6/2000 |
| WO | WO 99/45797 | * | 9/1999 |
| WO | WO 01/41775 A2 | * | 6/2001 |
| WO | WO 01/78529 A2 | * | 10/2001 |

OTHER PUBLICATIONS

Fitzpatrick D. Endothelium Dependent Vascular of Pycnogenol. J of Cardiovascular Pharm 32(4)509–515, 1998.*

Park Y. Activity of Monomeric, Dimeric and Trimeric Flavonoids . . . FEBS Letters 465(2,3)93–97, 2000.*

Packer L. Antioxidant Activity and Biologic Properties of a Procyanidin Rich Extract from Pine Bark, Pycnogenol. Free Radical Bio & Med 27(5/6)704–724, 1999.*

Kim S. Procyanidins in Crataegus Extract . . . Life Sciences 67(2)121–131, 2000.*

Print–out from selected portions of the Website www.arginmax.com, 1999.

Fabio Virgili, Hirotsugu Kobuchi & Lester Packer Nitrogen Monoxide (NO) Metabolism—Antioxidant Properties and Modulation of Inducible NO Synthase Activity in Activated Macrophages by Procyanidins Extracted From Pinus maritima (Pycnogenol), Flavonoids in Health and Disease, Ed. Catherine Rice–Evans and Lester Packer, by Marcel Dekker, Inc., 1998, Chapter 18, pp. 421–436.

David F. Fitzpatrick, Bettye Bing & Peter Rohdewald "Endothelium–Dependent Vascular Effects of Pycnogenol" Journal of Cardiovascular Pharmacology 32:0–00, 509–515, 1998 Lippincott–Raven Publishers.

Shiwen Wang, Duanjun Tan, Yusheng Zhao, Guankai Gao, Xue Gao, Lei Hu "The Effect of Pycnogenol on the Microcirculation, Platelet Function and Ishemic Myocardium in Patients with Coronary Artery Diseases" European Bulletin of Drug Research, vol. 7, No. 2, 1999, pp. 19–25.

* cited by examiner

*Primary Examiner*—Ralph Gitomer
(74) *Attorney, Agent, or Firm*—Gibbons, Del Deo, Dolan, Griffinger & Vecchione

(57) ABSTRACT

Use of proanthocyanidins as an active ingredient of a stimulator as a source of arginine and a source of nitric oxide in the treatment of erectile dysfunction. The active ingredient stimulates the endothelial NO-synthase enzyme, which acts as a catalyst for the synthesis of nitric oxide from its substrate L-arginine or its salts. The nitric oxide in turn activates theguanylyl cyclase, which leads to an increased development of cyclic guanosine monophosphate, which causes relaxation of smooth muscles. Blood vessel diameter may increase. The stimulator may also have Sildenafil or enzymes that inhibit an enzyme phosphodiesterase type5 from reducing an amount of the cyclic guanosine monophosphate. The substrate may be amino acid L-arginine, arginine salts or a dipeptide of arginine and aspartic acid.

17 Claims, No Drawings

RELIEVING SYMPTOMS OF ERECTILE DYSFUNCTION WITH PROANTHOCYANIDINS

CROSS-REFERENCE TO CO-PENDING PATENT APPLICATION

This is a utility patent application based on U.S. Provisional Patent Application Serial No. 60/207,520 filed May 26, 2000.

BACKGROUND OF THE INVENTION

1. Field of the Invention

The invention relates to the use of proanthocyanidins to stimulate the enzyme NO-synthase, which acts as a catalyst to release nitric oxide from L-arginine (or its salts). Such is advantageous in relieving symptoms of erectile dysfunction.

2. Discussion of Related Art

The normal penis reaction is based on a series of neurally mediated changes of bloodstream in the erectile tissue. The condition for an increased blood supply is the relaxation of smooth muscles in the erectile tissue. The relaxation takes place as follows:

As a result of sexual stimuli, the enzyme NO-synthase (NOS) gets activated in endothelial cells of the erectile tissue. This enzyme acts as a catalyst for the synthesis of nitric oxide (NO) from its substrate, amino acid L-arginine. The NO in turn activates the guanylyl cyclase which leads to an increased development of cyclic guanosine monophosphate (cGMP).

The cGMP causes relaxation of smooth muscles. Due to the reduction of cGMP by means of further enzymes, of which the phosphodiesterase type 5 (PDE type 5) is the most important one, the vasodilation can be rescinded.

The male impotence or erectile dysfunction is a widespread problem. It is the persistent inability of a man to get an erection and to maintain it long enough for satisfying sexual intercourse. The erectile dysfunction occurs mainly in older men; approximately 30% of men in their forties and 67% of men in their seventies are affected.

Present treatments comprise vacuum pumps, penis protheses, vascular surgery and the use of vasodilatory medicaments, such as Alprostadil, which can either be injected into the erectile tissue (Corpus cavernosum) or be brought into the urethra by means of an applicator. In March 1998, the American health authority FDA approved sildenafil (Viagra) as an oral treatment. In addition, there are other substances that are available that have the same, or substantially the same, mechanism of action as sildenafil. These other substances inhibit phosphodiesterase type 5 and/or prevent the decrease of cGMP.

Proanthocyanidins are homogeneous or heterogenous polymers consisting of the monomer units catechin or epicatechin, which are connected either by 4–8 or 4–6 linkages, to the effect that a great number of isomer proanthocyanidins exist. Typically, the procyanidin oligomers have a chain length of 2–12 monomer units.

Proanthocyanidins can be found in vegetable extracts, as well as in extracts of the bark of a maritime pine, the cones of cypresses, and the seeds and skin of grapes. A well-known product containing proanthocyanidins, which is available in trade as a preparation of a food supplement under the name Pycnogenol®, is an extract of the maritime pine bark (Pinus pinaster). The Pycnogenol® food supplement contains approximately 70–80% of proanthocyanidins and is a complex mixture of phenolic substances. It possesses a multitude of interesting and useful biochemical and pharmacological qualities. In particular, it is well known for its protecting effect against aging associated chronic diseases, such as atherosclerosis and its cardiovascular events such as stroke or heart infarction. Besides proanthocyanidins and its monomeric unit catechin, Pycnogenol® food supplement contains taxifolin and a wide range of phenolic acids, e.g. free acids like p-hydroxybenzoic acid, protoacatechic acid, vanillic acid, caffeic acid and ferulic acid as well as its glucosides and glucose esters. Most of the positive effects of Pycnogenol® are attributed to its antioxidant qualities.

Pycnogenol® food supplement deactivates superoxide radicals and hydroxyl radicals and inhibits the development of other oxygen radicals. In vitro, Pycnogenol® food supplement inhibits the peroxidization of LDL, the fat peroxidization in phospolipid liposomes and the fat peroxidization caused by t-butylhydroperoxide as well as the damage to cells induced by UV-B. As Pycnogenol® inhibits, in particular, the fat peroxidization of LDL, the risk of arteriosclerosis decreases. Moreover, Pycnogenol® food supplement contains procyanidins protecting collagen and elastin against enzymatical decomposition, which has a positive influence on the capillary resistance. The oral supply of this preparation to humans decreases the development of leg oedema.

It is known that some vegetable extracts containing proanthocyanidins show an endothelium-dependent relaxing activity (EDR). This has already been proven in red wine, grape juice and extracts of the peel of grapes ex vivo in aorta rings of rats (Fitzpatrick et al, Am., Physiol, 1993, 265 H774–8). Also, as concerns Pycnogenol® food supplement, such has also been found (Fitzpatrick et al: J Cardiovac, Pharmacol, Volume 32 Nr. 4, 1998) in that the fractions 3 preserved by sephadex LH-20 exclusion chromatography contained proanthocyanidins with a higher molecular weight showed the strongest EDR. Thus, it had been shown that proanthocyanidins increase the activity of the NO-synthase. The inhibition of the NO-synthase by well known inhibitors has been compensated by means of Pycnogenol® food supplement.

Sildenafil inhibits selectively the phosphodiesterase type 5 and thus prevents the decrease of cGMP. However, as Sildenafil does not promote the development of cGMP, but merely inhibits the decrease of existing cGMP, it is only effective, when there is already a quantity of cGMP sufficient enough for an erection, as for example in case of a strong sexual arousal. In case that there is an insufficient production of nitric oxide, which is necessary for stimulation of cGMP synthesis, the possibility exists that the quantity of cGMP is insufficient for an erection.

It is therefore desirable to develop a stimulation technique which does not interfere with the above mentioned chain reaction at the end, i.e., the prevention of the decrease of cGMP, but has a positive influence on the preceding reactions by stimulating NO-synthase and raising NO and cGMP concentrations.

SUMMARY OF THE INVENTION

One aspect of the invention resides in a stimulation technique that uses a combination of a source of nitric oxide, namely, amino acid L-arginine or its salts, and an active ingredient, namely, proanthocyanidins. Both the proanthocyanidins and the L-arginine or its salts are in therapeutically effective amounts to relieve symptons of erectile dysfunction and increase blood vessel diameter.

The proanthocyanidins are in an amount sufficient to stimulate the endothelial NO-synthase enzyme. Once stimulated, endothelial NO-synthase enzyme acts as a catalyst to synthesize nitric oxide from its substrate amino acid, L-arginine. Such a stimulator is necessary for the production of cGMP in larger amounts so that after neural activation, the development of nitric oxide may increase. The nitric oxide activates guanylyl cyclase, which increases cGMP and results in relaxation of smooth muscles.

The combination may also have sildenafil or an inhibitor that inhibits an enzyme phosphodiesterase type 5 from reducing an amount of the cGMP. In addition, both proanthocyanidins and L-arginine may be taken simultaneously. For instance, if both are in oral dosage form, both would be swallowed and be present within the stomach at the same time.

DETAILED DESCRIPTION OF THE INVENTION

Due to its content of proanthocyanidins, Pycnogenol® food supplement—and other vegetable extracts containing proanthocyanidins—is often used as a preventive measure against atherosclerosis and venous insufficiency. Up until the publication on Apr. 6, 2000 of German Patent Application No. 19845 314.0, it was not predictable that this food supplement could also specifically be used for the treatment of erectile dysfunction. Surprisingly, it turned out that the proanthocyanidins have a stimulating effect on the endothelial NO-synthase enzyme and thus serves as a stimulator.

The remedy preferably contains a mixture of proanthocyanidins from 50 to 100%, preferably 70%. The effective dosage of proanthocyanidins is 100 to 300 mg, preferably 200 mg.

The dosage amount refers to the daily dose for a male patient weighing 70 kg. For a male patient weighing less than 70 kg, the dosage needed to be effective would be lower and may be as low as 40 mg.

The well known pine bark extract Pycnogenol® food supplement is used as a proanthocyanidins containing remedy for the treatment of erectile dysfunction. In this instance, an application of 125 to 375 mg of Pycnogenol® food supplement is recommended for a 70 kg male.

As mentioned above, nitric oxide and nitric oxide-synthase play and important part in the erectile physiology. Studies with NOS-inhibitors, such as e.g. L-NORAG or L-NAME, which have been injected intracarvenally, revealed that an erection induced by electro-stimulations was suppressed. Being afterwards injected intravenally, the natural substrate for NOS, i.e., L-arginine, was able to partly recover the erection (Jung et al., Yondei Med. J. 1997, 3 (5), 261–269). The simultaneous injection of NOS-inhibitors and L-arginine led to a suppression of the effect of the inhibitors. Although L-arginine as a natural substrate of the endothelial NO-synthase enzyme is—as mentioned previously—able to partly decrease the effect of the NOS-inhibitors, it yet has not been taken into account as a remedy to promote the erectility.

According to the invention, the preferred remedy in addition to the proanthocyanidins also contains L-arginine (or its salts) as an effective component in an amount of at least 0.5 to 2 g. According to the invention, the combination of proanthocyanidins with L-arginine (or its salts) is particularly efficient. The L-arginine (or its salts) is the natural substrate for the nitric oxide synthase.

The active ingredients proanthocyanidins and L-arginine (or its salts) may be taken simultaneously that for maximum effect and benefit in treating erectile dysfunction. In addition, additional ingredients may include further pharmaceutically acceptable auxiliary or carrier substances, so far as they are, for example, used to get the active substance into the shape suitable for the desired medication.

Surprisingly, proanthocyanidins have a selective and specific effect on the blood vessels in the erectile tissue so that a remedy containing proanthocyanidins can preferably be given orally. As such, the remedy according to the invention thus exists in a form suitable for oral medication.

When taken with a known oral treatment remedy for erectile dysfunction, i.e., sildenafil (Viagra), proanthocyanidins help stimulate the endothelial NO-synthase enzyme, which serves as a catalyst for synthesis of nitric oxide from the substrate L-arginine or its salts. The released nitric oxide activates the guanylyl cyclase, leading to an increase in cGMP, which causes relaxation of smooth muscles, which in turn is the condition needed for increased blood supply. Thus, taking proanthocyanidins and L-arginine or its salts would complement the taking of sildenafil (Viagra) in the treatment of erectile dysfunction.

In addition, there are other substances that are available that have the same, or substantially the same, mechanism of action as sildenafil. These other substances, which may be considered inhibitors, are formed to inhibit phosphodiesterase type 5 and/or prevent the decrease of cGMP. The taking of proanthocyanidins and L-arginine (or its salts) would complement these other substances by countering the persistent inability of a man with erectile dysfunction to get an erection and to maintain it long enough for satisfying sexual intercourse.

A clinical study was conducted on forty participants who had erectile dysfunction. The study involved the effect of taking arginine asparatate, which is a salt of arginine with aspartic acid. One gram of arginine asparatate contains 566.85 mg of arginine.

The participants were grouped according to their variant of disturbed erection. The variants are in five categories: weakened, delayed, hesitating, losing and normal. The "weakened" variant signifies that the penis increases in size and becomes hard to a certain extent, but it is not enough to enter the vagina. The "delayed" variant signifies that if it is possible for the penis to become hard enough to enter the vagina, but such may require additional time. The "hesitating" variant signifies that before or after sexual contact, the erection is unstable and thus makes the sexual intercourse more difficult. The 'losing" variant signifies that during the love game there is good erection, but such is lost when trying to make contact or during intercourse. The "normal" variant signifies that no appreciable disturbed erection was present.

The clinical study was over three months. During the first month, only 3 doses of 1000 milligrams (mg) of arginine asparatate (Sargenor) were administered daily to each participant. By the end of the first month, there was improvement in erectile dysfunction in about 10% of the participants. During the second month, 2 doses of 40 mg of Pycnogenol® food supplement were administered daily to each participant, together with the 3 doses of 1000 mg of arginine asparatate. By the end of the second month, there was a statistically significant improvement of erectile dysfunction in 80% of the participants. During the third month, 3 doses of 40 mg of Pycnogenol® food supplement were administered daily to each participant, together with the 3 doses of 1000 mg of arginine asparatate. By the end of the third month, there was further improvement of the erectile dysfunction condition even for some of the participants who had not shown improvement during the second month. Overall, there was a statistically significant improvement of erectile dysfunction in 92% of the treated participants.

The following statistical analysis of the results from the clinical study calculate the probability of whether the observed differences between two treatments are statistically significant at a certain level.

| Variants of Disturbed Erection | Before n D | After 1 month A only n D | After 2 months A + P n D | After 3 months A + P n D |
|---|---|---|---|---|
| Weakened | 22 (55%) | 20 (50%) NS | 5 (12.5%)* | 2 (5%)** |
| Delayed | 12 (30%) | 10 (25%) NS | 2 (5%)* | 0 (0%)** |
| Hesitating | 2 (5%) | 4 (10%) NS | 1 (2.5%)* | 1 (2.5%)** |
| Losing | 4 (10%) | 4 (10%) NS | 0 (0%)* | 0 (0%)** |
| Normal | 0 (0%) | 2 (5%) NS | 32 (80%)*** | 37 (92.5%)** |

*$p < 0.05$
**$p < 0.01$
***$p < 0.001$

NS=not significant, n=number of participants/patients, D=percent distribution, A=arginine asparatate (each month at 3 doses×1000 mg daily), P=Pycnogenol® food supplement ($2^{nd}$ month at 2 doses×40 mg daily, $3^{rd}$ month at 3 doses×40 mg daily), p=probability.

In view of the clinical trial results, a dosage between 200 mg and 2 g of arginine per day together with a dosage of 60–360 mg of Pycnogenol® food supplement per day would be a therapeutically effective amount to relieve erectile dysfunction. According to the clinical study, the amount of arginine administered per day was about 1.7 grams, which is computed on the basis that 3 doses were taken of arginine asparatate, with each dose containing 566.85 mg of arginine.

The clinical trial used Caucasian men as the participants and the results show that 80–120 mg of Pycnogenol® food supplement is effective. For men with a lower body weight as compared to Caucasians, such as some Asians, positive results would be expected with a lower dosage. A dosage as low as 40 mg Pycnogenol® food supplement would be expected to be effective. Also, turning to the higher dosage level, one must consider that a small portion of the population is of tall height and overweight, which is expected to need a higher dosage to be effective. The highest dosage of Pycnogenol® food supplement used so far in other clinical trials (against edema of the lower legs) was 360 mg daily. The dosage of 300 mg is within the dosage range which had been tested clinically and one can expect that men with overweight and oversize need such a higher dose. Therefore, a dosage range of 40 mg–300 mg of Pycnogenol® food supplement would be effective, with the amount of the dosage that would be effective within the range depending upon the body weight of the man taking it.

Of course the same arguments hold for L-arginine and its salts. For men of lower body weight, a dosage of L-arginine or its salts as low as 200 mg would be effective and for men of greater body weight, a dosage of L-arginine or its salts as high as 2 grams would be effective. Thus, a range of 200 mg to 2 grams of L-arginine or its salts is effective depending upon the body weight and size of the man taking it. The effects of arginine are also dependent on the dosage and on the time elapsed between intake and sexual activity. The clinical study was based on daily intake only and did not specify any particular dosing intervals or prescribe a dosage regimen instruction for the patient participants to take, such as taking a certain amount of arginine at a defined period of time before sexual activity. Such instruction would be expected to better optimize the effectiveness of treating erectile dysfunction with these substances.

The dosage of Pycnogenol® food supplement may be 1–1.5 mg/kg and the dosage of L-arginine may be 15–40 mg/kg, preferably taken simultaneously to maximize their effectiveness in treating erectile dysfunction.

The reference to NO-synthase in this application is with respect to endothelial nitric oxide synthase, as opposed to inducible nitric oxide. The inducible nitric oxide synthase acts in an entirely different way and on a different place as the endothelial nitric oxide synthase.

The inducible nitric oxide synthase is produced in macrophages, white blood cells, which use the produced nitric oxide as one of their weapons against virus or bacteria, it is an inflammatory response. The endothelial nitric oxide regulates physiologically the vascular diameter and it is this enzyme which regulates erectile function.

Various changes and modifications may be made to the embodiments without departing from the spirit and scope of the present invention.

We claim:

1. A method of relieving symptoms of erectile dysfunction by stimulating nitric oxide (NO) synthase enzyme and releasing nitric oxide, comprising administering both proanthocyanidins and a substrate, which is a source of arginine and, subsequently, of nitric oxide; stimulating an endothelial NO-synthase enzyme with the proanthocyanidins; and releasing the nitric oxide from the substrate in response to the stimulated endothelial NO-synthase enzyme acting as a catalyst for synthesis of the nitric oxide, the proanthocyanidins and the substrate each being in therapeutically effective amounts to cause a sufficient amount of the nitric oxide to be released from the synthesis to relieve symptoms of erectile dysfunction.

2. The method according to claim 1, wherein the proanthocyanidins are in an amount of 40 to 300 mg.

3. The method according to claim 1, wherein the substrate is in an amount between 200 milligrams and 2 grams, inclusive.

4. The method according to claim 1, wherein the proanthocyanidins and the substrate are administered simultaneously.

5. The method according to claim 4, wherein the proanthocyanidins are in a dosage of 1–1.5 mg/kg and the substrate is in a dosage of 15–40 mg/kg.

6. The method according to claim 1, further comprising providing the proanthocyanidins in a form suitable for oral administration.

7. The method according to claim 1, wherein the stimulating is also carried out at the same time with sildenafil.

8. The method according to claim 1, wherein the stimulating is carried out while inhibiting an enzyme phosphodiesterase type 5 from reducing an amount of cyclic guanosine monophosphate.

9. The method according to claim 1, wherein the stimulating is carried out while preventing a decrease of cyclic guanosine monophosphate.

10. A composition to relieve symptoms of erectile dysfunction, the composition comprising a substrate as a source of arginine and, subsequently, for nitric oxide and a stimulator that includes proanthocyanidins to stimulate an endothelial NO-synthase enzyme, which serves as a catalyst for synthesis of the nitric oxide, the proanthocyanidins and the substrate being in therapeutically effective amounts to cause a sufficient amount of the nitric oxide to be released from the synthesis to relieve symptoms of erectile dysfunction.

11. The composition as in claim 10 in combination with sildenafil as a further active ingredient in a therapeutically effective amount to relieve the symptoms of erectile dysfunction and stimulate the endothelial NO-synthase enzyme.

12. The composition as in claim 10 in further combination with an inhibitor effective to inhibit an enzyme phosphodiesterase type 5 from reducing an amount of cyclic guanosine monophosphate.

13. The composition as in claim 10 in further combination with substances that are effective to prevent a decrease of cyclic guanosine monophosphate.

14. The composition as in claim 10, wherein the proanthocyanidins are in an amount within a range of 40 mg–300 mg, inclusive.

15. The composition as in claim 10, wherein the L-arginine or its salts is in an amount within a range of 200 mg and 2 grams, inclusive.

16. The composition as in claim 10, wherein the proanthocyanidins are in an amount within a range of 40 mg–300 mg, inclusive.

17. The composition as in claim 10, wherein the proanthocyanidins are in dosage of 1–1.5 mg/kg and the L-arginine or its salts are in a dosage of 15–40 mg/kg.

* * * * *